United States Patent [19]

Ciais et al.

[11] 4,238,451

[45] Dec. 9, 1980

[54] PROCESS AND DEVICE TO MEASURE THE ASPHALTENE CONTENT OF PETROLEUM PRODUCTS

[75] Inventors: Andre Ciais, Mornant; Andre Lambelin, St Pierre de Chandieu, both of France

[73] Assignee: Elf Union, France

[21] Appl. No.: 26,575

[22] Filed: Apr. 3, 1979

[30] Foreign Application Priority Data

Apr. 6, 1978 [FR] France ............................ 78 10210

[51] Int. Cl.³ .................... B01D 1/00; B01D 5/00; B01L 11/02
[52] U.S. Cl. ........................ 422/101; 23/230 HC; 202/161; 202/162; 202/169; 202/172; 203/DIG. 2; 203/98; 422/68; 422/280; 422/282
[58] Field of Search ................ 23/230 HC; 422/101, 422/280, 282; 203/DIG. 2, 98; 202/172, 161, 162, 169

[56] References Cited

U.S. PATENT DOCUMENTS

| | | | |
|---|---|---|---|
| 364,211 | 6/1887 | Brooke | 65/227 |
| 793,280 | 6/1905 | Curran | 65/323 |
| 3,423,192 | 1/1969 | Snover | 422/280 X |
| 3,607,662 | 9/1971 | Glover | 202/161 X |
| 3,849,649 | 11/1974 | Weiss | 422/101 X |
| 4,006,062 | 2/1977 | Bhuchor et al. | 422/101 X |

OTHER PUBLICATIONS

French Standard NF-T-60115, 5/5/70, "Dosage des Asphaltenes Precipites par l'Heptane Normal".

Primary Examiner—Michael S. Marcus
Attorney, Agent, or Firm—Bacon & Thomas

[57] ABSTRACT

An apparatus to measure the asphaltene content of petroleum products where a precipitation evaporator for the sample is surmounted by a condensing unit. Immediately below the precipitation evaporator is a filtering unit with a rinsing vapor inlet line for conveying washing liquid from a balloon-flask evaporator. The precipitation evaporator is also equipped with an adjustable flap for preventing fluid from passing to the filtering unit.

4 Claims, 9 Drawing Figures

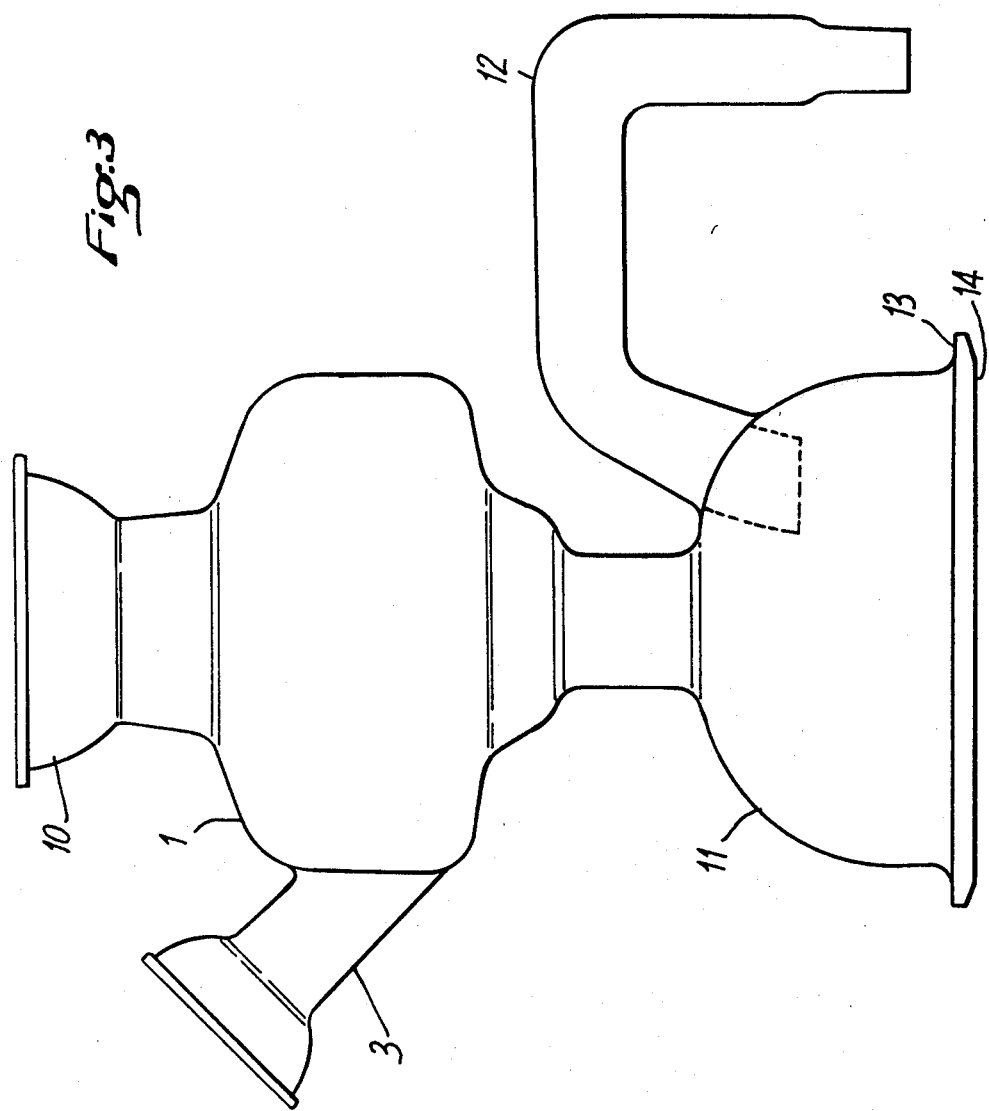

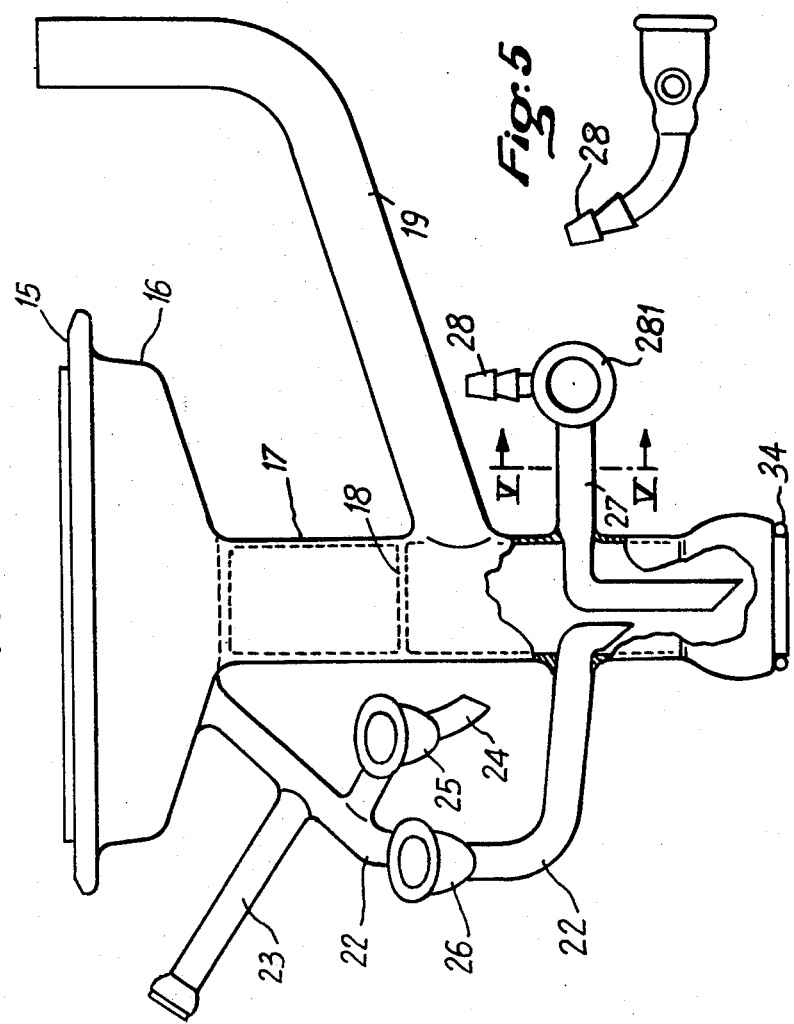
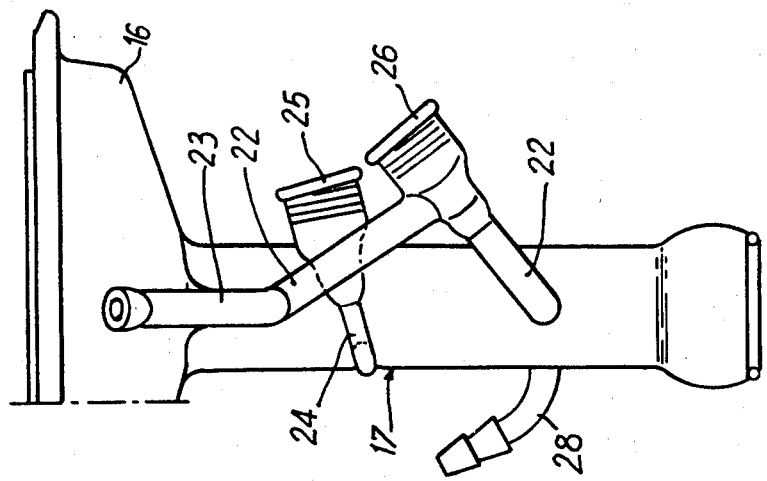
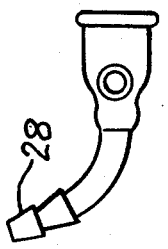

PROCESS AND DEVICE TO MEASURE THE ASPHALTENE CONTENT OF PETROLEUM PRODUCTS

This invention concerns a process and device to measure the asphaltene content of petroleum products.

French standard NF-T-60115 defines the asphaltene content of a petroleum product as the percentage weight of constituents insoluble in normal heptane under recommended test conditions, but soluble in hot benzene.

For conventional application of this standard, products for analysis are first treated at boiling point with n-heptane. After 2 hour's cooling, insolubles, consisting mainly of asphaltenes and certain paraffin constituents, are filtered out. What remains in the filter is again treated with hot normal heptane until the filtrate contains no further paraffin constituents. The asphaltenes that finally remain in the filter are then treated with benzene, and the solid that remains after evaporation of this benzene filtrate is regarded as the asphaltene content of the analysed product.

The apparatus used to apply this method therefore must comprise at least a balloon-flask, in which the first boiling treatment is performed, a filter unit in which insolubles resulting from the first treatment are separated out, an extraction apparatus to complete extraction of paraffin constituents remaining in the asphaltenes, and in which asphaltenes are dissolved with benzene, and finally an evaporation cup in which the residue is weighed to give the final result.

The disadvantage of this process and device is that it requires several manipulations by hand, using equipment involving several separate components. Transfer, cooling, filtering and washing operations introduce an element of imprecision and are very time-consuming. Furthermore, use of benzene as a solvent involves wastage, and it is difficult and dangerous to use.

This invention aims to overcome these drawbacks by offering a process and device for measuring the asphaltene content of petroleum products that are simple and inexpensive to apply, and allow much greater automation of filtering and washing operations, while having analysis time and considerably increasing measurement precision. The process also does away with the need for benzene and removes any risk of contact with vapourized solvent.

The invention concerns a process for measuring the asphaltene content of petroleum products in which, after treatment with n-heptane at boiling point, the resulting hot mixture is filtered immediately, insoluble matter is resubjected to reflux filtration, using n-heptane from the previous filtrate, heated to boiling point in the same container in which it has been collected, until the filtrate contains no further paraffin constituents, this container is replaced by a calibrated balloon-flask into which toluene is admitted, and heated to boiling point, reflux-condensed vapour is used to draw asphaltenes into the flask, and after the toluene has evaporated the flask is reweighed to measure the asphaltene content.

In one embodiment of the invention, the device to apply this process to measure the asphaltene content of petroleum products basically comprises a column in which the various treatment units are superimposed, including, from top to bottom, an upper evaporator surrounded by a heated casing and surmounted by a cooler, the base of this evaporator containing a down-pipe, normally closed off by a flap which can be operated from the top of the cooler, and a filter unit in two parts, roughly hemispherical in shape, holding a filter component between them, such as filter paper, metal gauze or sintered glass plate, the upper part of this filter unit being connected to the upper evaporator by the down-pipe and containing a washing-vapour inlet tube at the side, and the lower part of the unit, which contains a down-pipe for liquids, being supported on a hollow column, which surmounts an interchangeable lower evaporator, and the side of which contains the inlet opening for the liquid down-pipe and a washing-vapour outlet tube, connected to the washing-vapour inlet tube in the side of the filter unit.

It will be easier to understand the invention from the following description, illustrated by the accompanying figures:

FIGS. 2 to 7 are more detailed views of the different parts of the device shown in FIG. 1;

Figure 1:
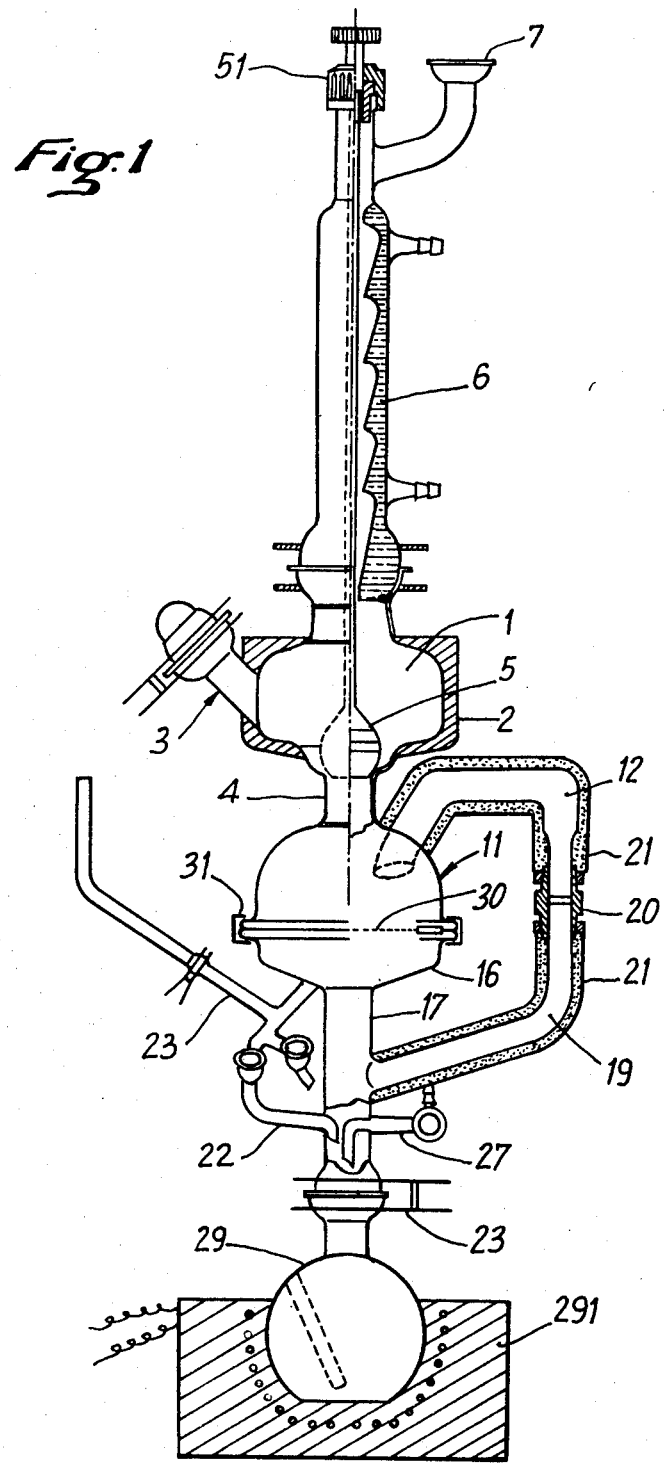
FIG. 1 is a partly cross-sectional front view of the device for this new process to measure the asphaltene content of petroleum products.

FIG. 1 shows a precipitation evaporator 1 surrounded by a heated casing 2 and with a tube 3 at the side through which heptane and the sample for analysis are admitted. At the base of evaporator is the opening to a down-pipe 4 bounded by a female ground surface into which fits the flap 5, raising and lowering of which are controlled by a mechanism 51 at the top.

Figure 2:
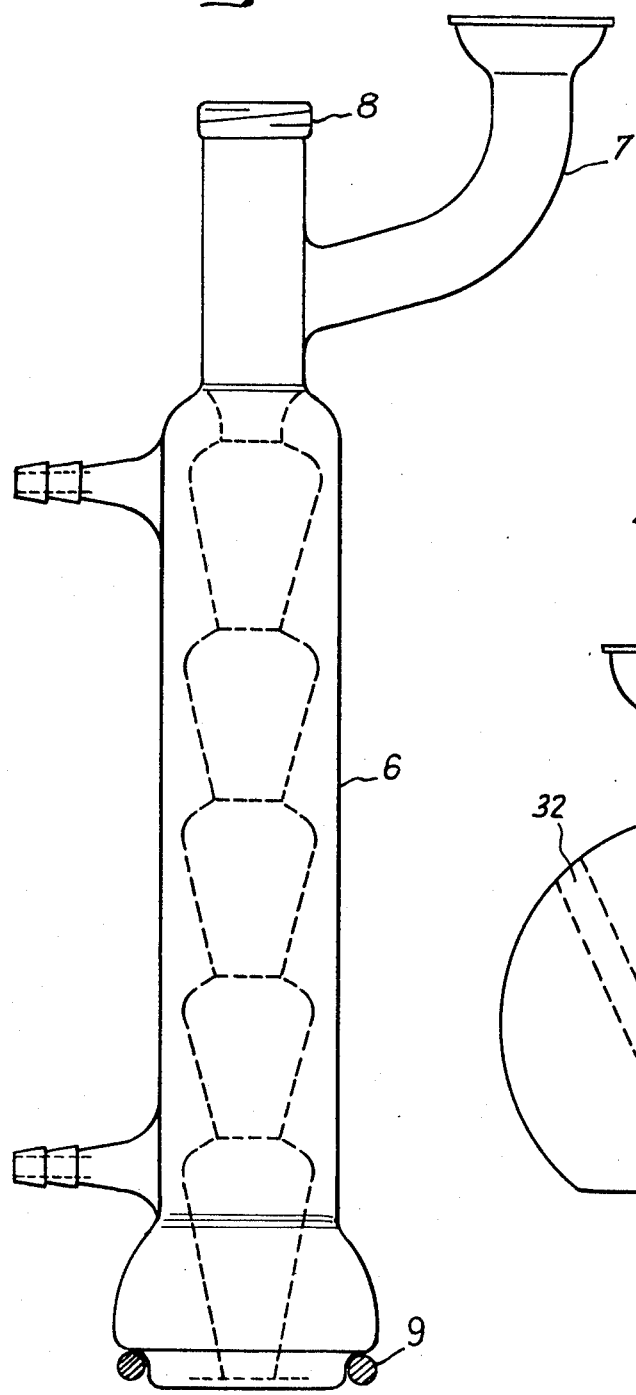

The precipitation evaporator 1 is surmounted by a cooler 6, shown in greater detail in FIG. 2. This is a conventional globe condenser with an atmospheric-release tube 7 at the side. The upper end 8 of the cooler is threaded, so that the mechanism to operate the flap 5 can screw on to it. A sealing ring 9 fits between the lower end of the cooler 6 and the top of the neck 10 of evaporator 1.

FIG. 3 shows, immediately below the precipitation evaporator 1, the top part of the filter unit, consisting of a hemispherical cap 11, into the side of which opens a half-tube 12 of rising washing vapour. This cap 11 has a projecting lower rim, and the bottom surface 14 is ground so that it will fit hermetically against a matching surface 15 on the lower part of the filter unit.

FIG. 4 shows the lower part of the filter unit, comprising a cup 16 on top of a hollow column 17. Two thirds way up, this column 17 is blocked by a diaphragm 18. A half-tube 19 runs out of the side of column 17, and is connected to half-tube 12 by a connector 20. These two half-tubes 12 and 19, which convey washing vapour upwards, are surrounded by a layer 21 of heat-insulating material.

A tube 22 runs from cup 16 into column 17. It contains an atmospheric-release branch-pipe 23 at the side, and another branch-pipe 24 ending in a tap 25 to remove solvent condensates. Below the starting point of branch-pipes 23 and 24 in tube 22 there is another tap 26. When this is opened, liquids in cup 16 can run into column 17.

A right-angled tube 27 opens into column 17. It is connected to a nitrogen inlet 28 with a tap 281; to help evaporate solvents and dry precipitates without asphaltenes being oxidized in a lower evaporator 29 surrounded by a heated casing 291.

A filter 30 is inserted between the ground surfaces 14 on the edge of cap 11 and 15 on the edge of cup 16, with rings to ensure that the join is completely hermetic. It is held by a clamping ring 31. When a sintered glass plate is used as the filter, the appliance is in one piece, both caps being welded to the plate, and the side tube is also in one piece.

Figure 7:
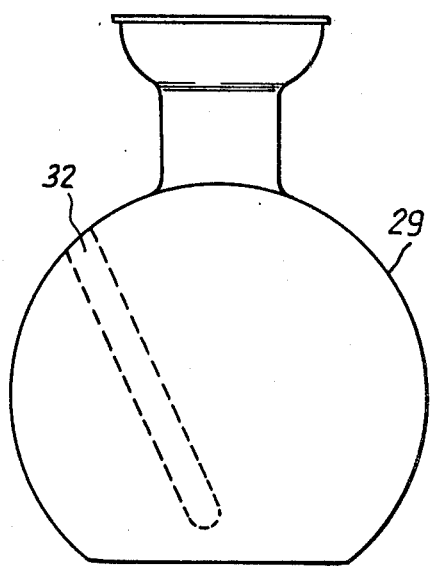

FIG. 7 shows the lower evaporator 29, comprising a flat-bottomed balloon-flask of Pyrex glass, with a thermometer tube 32. During the process it is clipped to the bottom of column 17 by means of a clamping ring 33, with a sealing ring 34.

This asphaltene-measuring apparatus works in the following way.

All grease and moisture are carefully removed from the various items of equipment before they are assembled. A filter is placed between cap 11 and cup 16, and the ring 31 is tightened.

Figure 8:
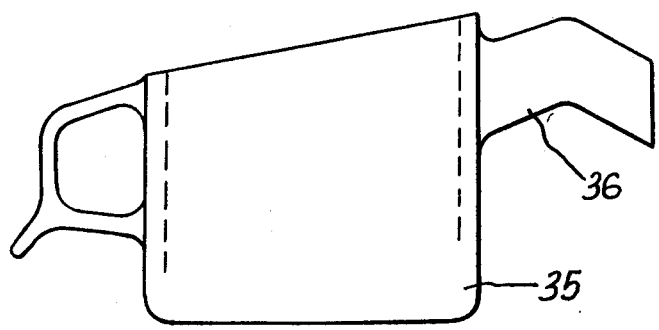
FIGS. 8 and 9 show the sampling container used with the device, and a detailed view of the structure of its spout.
Figure 9:
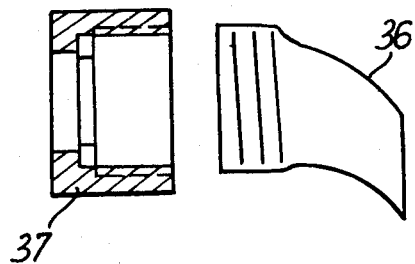

FIGS. 8 and 9 show the container 35 used to add the sample for analysis. This container is in the shape of a watering-can, with a special spout 36, which normally curves downwards. When the sample has been poured into the equipment, the spout 36 can be turned in its base 37 on container 35, so that it curves upwards, allowing the viscous drops to be recovered, and thereby preventing any wastage.

Grease and moisture are also removed from this container 35, and approximately 12 grams of the sample are placed in it. The weight P1 of container and sample is recorded.

When the equipment is fully assembled, nitrogen is blown through with valve 5 open, after which it is closed. Taps 25 and 281 are kept shut, and tap 26 is kept open. 300 ml normal heptane is then poured into the upper evaporator 1 through tube 3, followed by the contents of container 35. Tube 3 is blocked. The weight P2 of the empty container is recorded, giving the weight of the sample for analysis P2-P1.

The heated casing 2 is turned on and reflux boiling maintained in the upper evaporator 1 for 30 minutes. The heating is then turned off, and valve 5 raised immediately by screwing the control mechanism 51 down slowly. The heptane/asphaltene hydrocarbon mixture drops into cap 11 on to filter 30, and the filtrate passes through tube 22 into column 17 and finally into lower evaporator 29. This evaporator is weighed before being fitted, and its weight P3 recorded.

The heated casing 291 is turned on to heat the filtrate in lower evaporator 29 to boiling point, with tap 26 still kept open. The heptane vapour rises through tubes 19 and 12 and condenses in cap 11, washing the asphaltene precipitate on filter 30. If necessary at this stage of the operation, valve 5 can be left open so that vapour penetrates into upper evaporator 1, condensing there or in cooler 6 and thereby completing washing of the evaporator. The heptane heating system is stopped and heated casing 291 disconnected, once the filtrate runs clear and limpid into cup 16 and tube 22.

The lower evaporator is then replaced by another evaporator 29a, the weight P4 of which has also been recorded, and nitrogen is again blown through the equipment. 300 ml toluene is poured into evaporator 29a, with tap 26 still open. The heated casing 291 is reconnected and, as earlier, the toluene vapour reaches the upper evaporator 1 and cap 11 to dissolve any asphaltenes still remaining there. Asphaltenes remaining on the filter are also dissolved, and toluene washing is continued until the filtrate runs clear and limpid.

While the toluene is at boiling point, tap 26 is closed and tap 25 opened, to recover pure toluene in a flask.

When the temperature exceeds 110° C., in other words when the toluene is almost completely evaporated and removed from the apparatus, tap 281 is opened, and nitrogen admitted at a pressure of 0.1 bars above atmospheric pressure. At the same time, the heating inside casing 291 is reduced, so that evaporator 29 is no longer heated by contact but by radiation. Nitrogen pressure is raised gradually to 0.5 bars, for long enough to dry completely the asphaltenes collected in evaporator 29A. The evaporator is then cooled and weighed, and its new weight P5 recorded.

The result of the experiment is expressed by the formula:

$$\% \text{ weight of asphaltenes } (Pa) = \frac{(P5 - P4) \times 100}{(P2 - P1)}$$

Experience shows that this is a very precise method, offering very good repeatibility and reproducibility.

The intermediate stages of waiting for cooling and of decanting are eliminated, and the filter can be used repeatedly without dismantling, thereby saving a considerable amount of time.

Without any departure from the spirit of this invention, the device can naturally be used for any other quantitive analysis that requires, for example, precipitation followed by redissolution of the precipitate with another solvent.

What is claimed is:

1. An apparatus for quantitative analysis of a sample requiring precipitation and evaporation which comprises in a columnar arrangement from top to bottom; condensing means connected to an upper portion of a first evaporator means, said first evaporator means having heating means, sample inlet means, and basal outlet means, said basal outlet means comprising an opening connected to a first downpipe for refluxed sample carrying liquid, said opening fitted with adjustable closing means; said downpipe connected to filter means for receiving and filtering said refluxed liquid comprising two parts roughly hemispherical in shape forming an upper and lower portion with an interposed filter; said upper portion having a washing-vapor inlet tube, said lower portion having a downpipe for washing liquids; said filtering means supported by a column which surmounts an interchangeable lower evaporator and heating means, at least a portion of said supporting column being hollow and communicating with said lower evaporator, said hollow column portion having connecting means which connect said hollow column portion with said downpipe and washing-vapor intlet tube of said filter means to provide a circuitous route for a washing fluid between said lower evaporator and said filter means through said filter.

2. The apparatus of claim 1 wherein the filter is filter paper, metal gauze or sintered glass.

3. The apparatus of claim 1 which further comprises a gas inlet tube connected to said hollow column portion.

4. The apparatus of claim 1 wherein said downpipe for washing liquids further comprises branch pipes connected thereto for solvent removal and atmospheric venting.

* * * * *